United States Patent [19]

Garcia et al.

[11] 4,147,870

[45] Apr. 3, 1979

[54] 1-ARYLAMIDOETHYL, 4-SULFONYLPIPERAZINES

[75] Inventors: Antonio A. García, Guadalajara; Juan R. C. Ruiz; Juan B. Lozano, both of Madrid, all of Spain

[73] Assignee: Laboratorios Liade, S.A., Madrid, Spain

[21] Appl. No.: 852,850

[22] Filed: Nov. 18, 1977

Related U.S. Application Data

[63] Continuation-in-part of Ser. No. 687,947, May 19, 1976, abandoned.

[51] Int. Cl.² .................................. C07D 241/04
[52] U.S. Cl. .................................... 544/383; 424/250
[58] Field of Search .................................. 544/383

[56] References Cited

PUBLICATIONS

Lange et al., Jour. Pharm. Sci., vol. 51, No. 1, 1962, pp. 32–35.

Primary Examiner—Paul M. Coughlan, Jr.

[57] ABSTRACT

This invention is directed to a novel series of piperazine derivatives which have shown some interesting pharmacological activities: analgesic activity, action on the cardiovascular system, and a specific bronchodilator action on the experimental asthma.

1 Claim, No Drawings

1-ARYLAMIDOETHYL, 4-SULFONYLPIPERAZINES

This is a continuation-in-part application of U.S. patent application Ser. No. 687,947, filed May 19, 1976, now abandoned.

This invention is directed to a novel series of piperazine derivatives having the general structural formula

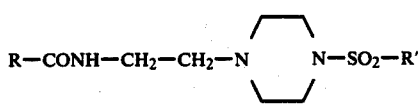

(I)

wherein R, and R' may be:

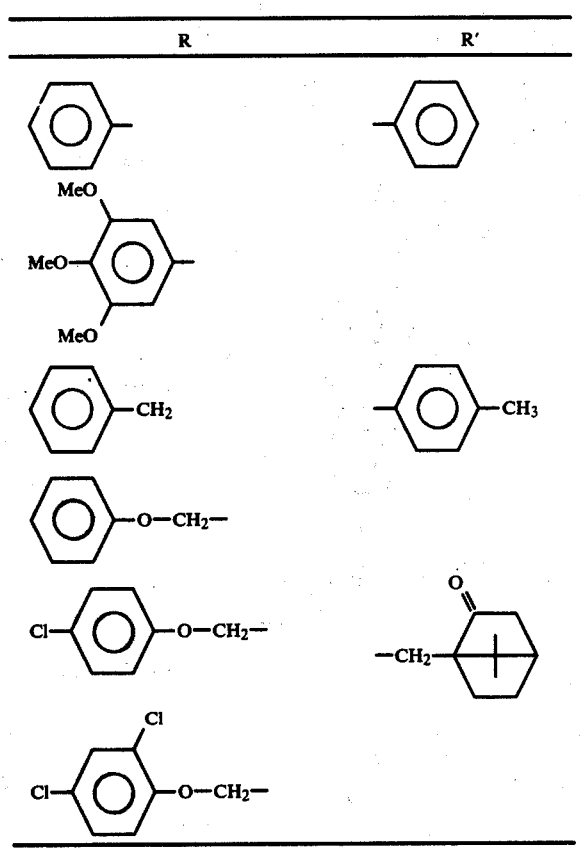

These compounds have shown some interesting pharmacological activities: analgesic activity, action on the cardiovascular system, and a specific bronchodilator action on the experimental asthma.

The cardiovascular action has been shown as stimulating in some cases and depressing in some others.

Beside these properties, an important local anesthetic action and a remarkable anticholinergic activity have been noted.

In all cases the active doses are far-away from the toxic doses.

The initial materials used in the preparation of the final product are:

Acylaziridene 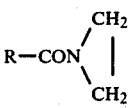

Sulfonyl piperazine 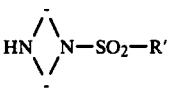

The acylaziridine is prepared following one of several conventional methods existing in the following bibliography, depending upon each particular case.

METHOD A

The aziridine, dissolved in benzene, is added to a water-ice mixture containing an inorganic base (NaOH, for example). Afterwards, a chloride acid is slowly added and the reaction mixture is extracted with benzene. The organic phase is dried and evaporated and the residue of acylaziridine is recrystallized in petroleum ether.

METHOD B

The chloride acid is slowly added to a cold solution of aziridine in acetone and triethylamine. The hydrochlorate of triethylamine is eliminated by filtration and the acetonic solution evaporates, upon drying, and a residue of acylaziridine is obtained.

METHOD C

The chloride acid is added to a solution of an excess of aziridine in acetone. The hydrochlorate of the excess of aziridine is filtered, and the acetonic solution evaporates, upon drying, and the corresponding acylaziridine is obtained.

BIBLIOGRAPHY

J Am. Chem. Soc., 81, 2202–2204 (1959)
J. Chem. Soc., 1923 (1948)
Ber., 32, 2036–2038 (1899)
Bull. Soc. Chim. Belg., 55, 54 (1946)

The obtention of sulfonylpiperazine is carried out by the process described in the subject application.

The analgesic activity is one of the pharmacological actions that have been most outstanding in the study of the different 1-arilamidoethyl-4-sulfonylpiperazine.

The methods of study of the analgesia are made through chemical stimulations in mice and electrical stimulations in rabbits.

The chemical stimulation consists in the intraperitoneal injection of an irritating substance that causes a characteristic contortion response in the form of contractions in the abdomen, twisting of the trunk and extension of the rear legs. The contractions of the animal are observed during 20 minutes.

The product is administered in an oral way, 30 minutes before the irritating substance.

The analgesia is determined by:

$$\% \text{ analgesia} = \frac{\text{temoin contractions} - \text{treated contractions}}{\text{temoin contractions}} \times 100$$

The method of Paeile and collaborators (1962) consists in measuring the threshold of the electrical stimulation of the dental pulp in the rabbit, having previously formed two cavities in the incisors with the placement of copper electrodes therein. A voltage is applied until the production of characteristic masticatory movements. This level is to be the threshold value.

The administration of analgesics will raise the temoin threshold value, considering as 100% protection that dosage with which the animal resists 10 volts more than the temoin.

The product is administered orally, through a gastric probe.

SIEGMUND and collaborators (1957)
KOSTER and collaborators (1952)
PAEILE and collaborators (1962)

In the following table, the results found for the dose of 25 mg/kg p.o. for the different compounds of this series are expressed.

| FORMULA | Code | Activity |
|---|---|---|
| Cl—C$_6$H$_4$—O—CH$_2$—CO—NH—CH$_2$—CH$_2$—N(piperazine)N—SO$_2$—C$_6$H$_4$—CH$_3$ | LIA-1045 | 0 |
| Cl—C$_6$H$_4$—O—CH$_2$—CO—NH—CH$_2$—CH$_2$—N(piperazine)N—SO$_2$—CH$_2$—(camphor) | LIA-1046 | 0 |
| Cl—C$_6$H$_4$—O—CH$_2$—CO—NH—CH$_2$—CH$_2$—N(piperazine)N—SO$_2$—C$_6$H$_5$ | LIA-1065 | 0 |
| C$_6$H$_5$—O—CH$_2$—CO—NH—CH$_2$—CH$_2$—N(piperazine)N—SO$_2$—C$_6$H$_4$—CH$_3$ | LIA-1041 | 19 |
| C$_6$H$_5$—CO—NH—CH$_2$—CH$_2$—N(piperazine)N—SO$_2$—C$_6$H$_4$—CH$_3$ | LIA-978 | 25 |
| C$_6$H$_5$—CO—NH—CH$_2$—CH$_2$—N(piperazine)N—SO$_2$—CH$_2$—(camphor) | LIA-984 | 26 |
| C$_6$H$_5$—CH$_2$—CO—NH—CH$_2$—CH$_2$—N(piperazine)N—SO$_2$—C$_6$H$_4$—CH$_3$ | LIA-1044 | 26 |
| (3,4,5-tri-CH$_3$O)C$_6$H$_2$—CO—NH—CH$_2$—CH$_2$—N(piperazine)N—SO$_2$—CH$_2$—(camphor) | LIA-1009 | 30 |
| C$_6$H$_5$—CO—NH—CH$_2$—CH$_2$—N(piperazine)N—SO$_2$—C$_6$H$_5$ | LIA-1052 | 30 |
| C$_6$H$_5$—O—CH$_2$—CO—NH—CH$_2$—CH$_2$—N(piperazine)N—SO$_2$—C$_6$H$_5$ | LIA-1054 | 32 |
| (3,4,5-tri-CH$_3$O)C$_6$H$_2$—CO—NH—CH$_2$—CH$_2$—N(piperazine)N—SO$_2$—C$_6$H$_4$—CH$_3$ | LIA-993 | 34 |

Also considered as products of interest are acetylsalicylic acid, phenylbutasone and dextropopoxyphene. The more active products of this chemical series have exceeded in analgesic activity all the standard products.

The following sequence can be considered as an example of activities: acetylsalicylic acid < phenylbutasone < LIA-1009 < dextropopoxyphene.

The cardiovascular activity of this series can be represented by LIA-1009.

The study has been made on the electrocardiogram, the arterial pressure, the dp/dt and the cardiac frequency, and these tests allow observing the variations that can take place when the experience is made with the product to study and reach some conclusions on its action on the cardiovascular system.

*Arterial pressure.* Measured by placing a probe on a peripheric artery and connecting it to a pressure sensor that will carry the received impulses up to the polygraph, where its value is graphically registered.

*dp/dt.* For measuring the dp/dt, an electronic differentiator is used in connection with the pressure preamplifier.

When the product is administered intraduodenally, it allows obtention of the variations that the pressure can vary with respect to time.

*Cardiac frequency.* The cardiac frequency and its derivations during all the tests are graphically collected with the aid of a tachometer.

*Electrocardiogram.* Obtained in derivation II, it is possible to observe the changes that take place during all the experience.

Arch. Int. Pharmacodyna., 179, 284 (1969).

The results are expressed in the following table:

| Cardiovascular action | Dose | |
|---|---|---|
| | 10 mg/kg oral | 25 mg/kg oral |
| Arterial pressure | ↑ 9% | ↑ 14% |
| E.C.G. | = | = |
| dp/dt | ↓ 20% | ↓ 43% |
| Cardiac frequency | ↓ 27.5% | ↑ 20% |

A notable diminution in the dp/dt. is observed.

The products of this series have not demonstrated antiinflammatory or antipyretic activity, it being proven that the analgesic action is of central origin.

In all the cases the $DL_{50}$ administered in an oral way has been very superior up to dosages of 1000 mg/kg.

A slight central depressor action has been observed in these products.

DESCRIPTION OF THE PROCESS

The compounds are synthetized following a single-step method, by reaction of the corresponding acyl-aziridine with the monosulfonyl derivative of piperazine:

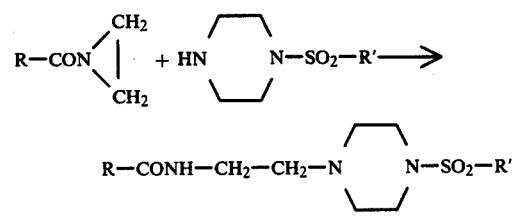
(I)

An alternate route to the preparation of compounds (I) comprises the reaction between a N-acyl, tosyloxy-ethylamine and a monosulfonylpiperazine:

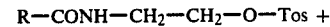

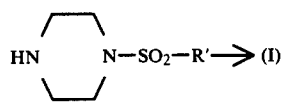

GENERAL METHOD 0.01 Mol of the monosulfonylpiperazine and 0.013 Mol of the acylaziridine are dissolved in dry toluene. The solution is refluxed until all the monosulfonylpiperazine has reacted as shown by TLC control of the reaction mixture. (Silicagel F-254 plate; solvent: Benzene/Methanol (9:1). The compound precipitates upon cooling the reaction mixture in an ice-bath.

EXAMPLE 1

(1-benzamidoethyl,4-benzenesulfonyl)piperazine

Yield: 65%
Crystallized from methanol
M.P. = 82°–85° C.

EXAMPLE 2

(1-benzamidoethyl,4-p-toluensulfonyl)piperazine

Yield: 60%
Crystallized from methanol
M.P. = 163°–164° C.

EXAMPLE 3

(1-benzamidoethyl,4-camphorsulfonyl)piperazine

Yield: 80%
Crystallized from methanol
M.P. = 141°–143° C.

EXAMPLE 4

[1-(3',4',5'trimethoxy-benzamidoethyl),4-benzenesulfonyl]piperazine

Yield: 41%
Crystallized from toluene
M.P. = 127°–128° C.

EXAMPLE 5

[1-(3',4',5'-trimethoxybenzamidoethyl),4-toluenesulfonyl]piperazine

Yield: 78%
Crystallized from methanol
M.P. = 168°–170° C.

EXAMPLE 6

[1-(3',4',5'-trimethoxybenzamidoethyl),4-camphorsulfonyl]piperazine

Yield: 89%
Crystallized from methanol
M.P. = 83°–85° C.

EXAMPLE 7

[1-Phenylacetamidoethyl,4-benzenesulfonyl]piperazine

Yield: 50%
Crystallized from xylene
M.P. = 98°–100° C.

EXAMPLE 8

(1-Phenylacetamidoethyl,4-p-toluensulfonyl)piperazine

Yield: 35%
Crystallized from toluene
M.P. = 111°–112° C.

EXAMPLE 9

(1-Phenylacetamidoethyl,4-camphorsulfonyl)piperazine

Yield: 40%
Crystallized from xylene
M.P. = 95°–98° C.

EXAMPLE 10

(1-Phenoxiacetamidoethyl,4-benzenesulfonyl)piperazine

Yield: 51%
Crystallized from toluene
M.P. = 110°–113° C.

EXAMPLE 11

(1-Phenoxyacetamidoethyl,4-p-toluensulfonyl)piperazine

Yield: 40%
Crystallized from methanol
M.P. = 122°–124° C.

EXAMPLE 12

(1-Phenoxyacetamidoethyl,4-camphorsulfonyl)piperazine

Yield: 50%
Crystallized from toluene
M.P. = 152°–154° C.

EXAMPLE 13

[1-(4'-chlorophenoxyacetamidoethyl),4-benzenesulfonyl]piperazine

Yield: 50%
Crystallized from methanol
M.P. = 137°–138° C.

EXAMPLE 14

[1-(4'-chlorophenoxyacetamidoethyl),4-p-toluenesulfonyl]piperazine

Yield: 70%
Crystallized from methanol
M.P. = 142°–143° C.

EXAMPLE 15

[1-(4'-chlorophenoxyacetamidoethyl),4-camphorsulfonyl]piperazine

Yield: 60%
Crystallized from
M.P. = 134°–136° C.

EXAMPLE 16

[1-(2',4'-dichlorophenoxyacetamidoethyl),4-benzenesulfonyl]piperazine

Yield: 40%
Crystallized from methanol
M.P. = 120°–122° C.

EXAMPLE 17

[1-(2',4'-dichlorophenoxyacetamidoethyl),4-p-toluensulfonyl]piperazine

Yield: 70%
Crystallized from methanol
M.P. = 140°–142° C.

EXAMPLE 18

[1-(2',4'-dichlorophenoxyacetamidoethyl),4-camphorsulfonyl]piperazine

Yield: 70%
Crystallized from methanol
M.P. = 131°–132° C.

What is claimed is:
1. A method of synthesizing piperazine derivatives comprising the step of reacting the corresponding acyl-aziridine with the monosulfonyl derivative of piperazine according to the reaction

$$R-CON\begin{matrix}CH_2\\ \\CH_2\end{matrix} + HN\diagdown\!\!\diagup N-SO_2-R' \longrightarrow$$

$$R-CONH-CH_2-CH_2-N\diagdown\!\!\diagup N-SO_2-R',$$

wherein:
R is selected from the group consisting of

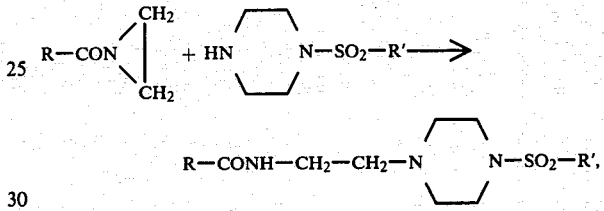

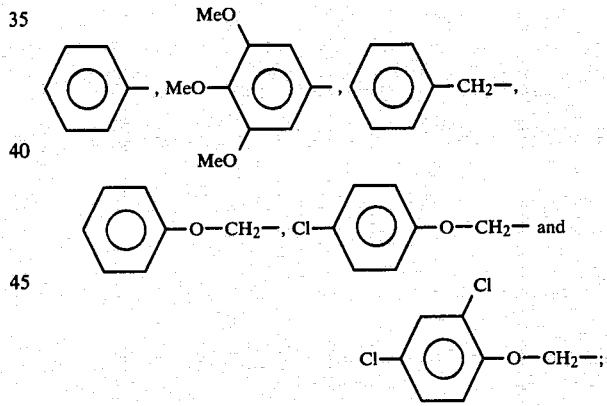

and
R' is selected from the group consisting of

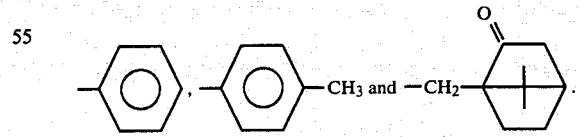

* * * * *